United States Patent [19]

Yazawa et al.

[11] Patent Number: 5,436,269

[45] Date of Patent: Jul. 25, 1995

[54] METHOD FOR TREATING HEPATITIS

[75] Inventors: Kazunaga Yazawa, Sagamihara; Tomohito Hamasaki; Hirofumi Taki, both of Toyama; Kiyosi Kondo, Yamato; Mitihiro Sugano, Fukuoka; Ikuo Ikeda, Munakata, all of Japan

[73] Assignee: Sagami Chemical Research Center, Tokyo, Japan

[21] Appl. No.: 87,708

[22] PCT Filed: Nov. 13, 1992

[86] PCT No.: PCT/JP92/01486

§ 371 Date: Nov. 8, 1993

§ 102(e) Date: Nov. 8, 1993

[87] PCT Pub. No.: WO93/09772

PCT Pub. Date: May 27, 1993

[30] Foreign Application Priority Data

Nov. 14, 1991 [JP] Japan ................ 3-325019
Jun. 3, 1992 [JP] Japan ................ 4-166724

[51] Int. Cl.[6] ................ A61K 31/225; A61K 31/20
[52] U.S. Cl. ................ 514/547; 514/560
[58] Field of Search ................ 514/547, 560; 554/465

[56] References Cited

U.S. PATENT DOCUMENTS 4,513,008 4/1985 Revici et al. ................ 514/560
4,607,052 8/1986 Mendy et al. ................ 514/547
4,692,280 9/1987 Spinelli et al. ................ 260/420

FOREIGN PATENT DOCUMENTS 0175468 3/1986 European Pat. Off. .
0347056 12/1989 European Pat. Off. .
7964 6/1970 France .
56-122312 9/1981 Japan .
63-297342 12/1988 Japan .
2-200165 8/1990 Japan .
2218904 11/1989 United Kingdom .

OTHER PUBLICATIONS

Chemical Abstracts (110:134018K) Vogeler et al. 1989.
Chemical Abstracts, vol. 107, No. 9, AN 75485v, 1987, V. M. Mokhov, et al., "Fatty Acid Composition of Liver Tissue Lipids in Chronic Hepatitis, Cirrhosis and Fatty Hepatosis".
Journal of Clinical Biochemistry and Nutrition, vol. 6, No. 3, pp. 213-220, May 1989, M. Okita, et al., "Beneficial Effect Of Polyunsaturated Fatty Acid-Supplemented Diet On Altered Composition Of Plasma Fatty Acids In Patients With Liver Cirrhosis".
Metabolism, vol. 34, No. 10, pp. 900-905, Oct. 1985, S. Wong, et al., "Reduced Triglyceride Formation From Long-Chain Polyenoic Fatty Acids In Fat Hepatocytes".
Biochimica et Biophysica Acta, vol. 962, No. 3, pp. 337-344, 1988, M. L. Garg, et al., "Fish Oil Reduces Cholesterol And Arachidonic Acid Content More Efficiently In Fats Fed Diets Containing Low Linoleic Acid To Saturated Fatty Acid Ratios".
Ann. Nutr. Metab., vol. 34, pp. 288-296, 1990, M. Saito, et al., "Influence Of Different Types And Levels Of Dietary Lipids On Liver Microsomal Mixed Function Oxidase System In Rats".
FASEB, vol. 4, No. 3, pp. A507, 1990, J. Van Aerde, et al., "Eicosapentaenoic (EPA) And Docosahexaenoic Acid (DHA) Prevent Cholestatic Jaundice In The Intravenously (IV) Fed Neonate".

Primary Examiner—Marianne M. Cintins
Assistant Examiner—K. Weddington
Attorney, Agent, or Firm—Oblon, Spivak, McClelland, Maier, & Neustadt

[57] ABSTRACT

A drug for hepatic diseases, particularly an ameliorant for hepatic functions and a drug for hepatitis, containing docosahexaenoic acid or a derivative thereof (DHA) as an active ingredient. The DHA as the active drug ingredient, though also taking part in the metabolism of cholesterol formed in vivo and exuding into the plasma, mainly metabolizes that cholesterol specifically which is accumulated in hepatic microsomes as a result of hypometabolism or dysbolism to thereby bring about the recovery of flexibility of a microsome lipid membrane, thus enhancing the enzymatic activity, and to significantly reduce a triglyceride, thus being prospective as an ameliorant for hepatic functions in treating fatty liver, hepatic cirrhosis, etc. The invention also provides a drug for hepatitis, which can inhibit the induction of hepatitis which is one of the factor causative of chronic hepatitis, hepatocirrhosis, hepatocellular carcinoma, hepatic insufficiency, etc.

2 Claims, No Drawings

METHOD FOR TREATING HEPATITIS

This application is a 371 of PCT/JP92/01486 filed Nov. 13, 1992.

TECHNOLOGICAL FIELD

The present invention relates to a drug for hepatic diseases, especially an ameliorant for hepatic function and a drug for hepatitis, which contains docosahexaenoic acid as the active ingredient.

BACKGROUND ART

Docosahexaenoic acid and its derivatives are known, in their mixed form, as a remedy for complications of diabetes (Japanese Patent Application Laid Open (Kokai) No. 60-24610) or hemorrhoid (Japanese Patent Application Laid Open (Kokai) No. 61-24518), a stimulant of lipoxygenase metabolism (Japanese Patent Application Laid Open (Kokai) No. 63-230632), an ameliorant for brain functions (Japanese Patent Application Laid Open (Kokai) No. 1-27982), an anticancer agent (Japanese Patent Application Laid Open (Kokai) No. 1-153629), a remedy for capsular nephritis (Japanese Patent Application Laid Open (Kokai) No. 2-235811), and an antiarrhythmic agent (Japanese Patent Application Laid Open (Kokai) No. 4-29928).

Polyene phosphatidyl choline preparation is generally accepted as a remedy for hepatitis. Mevalotin or mevinolin type compounds have been used for inhibiting biosynthesis of cholesterol. Linoleic acid and linolenic acid have been widely used for removing cholesterol in blood serum and for preventing arteriosclerosis.

Among a few drugs for hepatic diseases, polyene phosphatidyl choline preparation has been used for a long time but possesses only mild cholesterol reducing efficacy, though it is almost satisfactory in its safety. The preparations of mevalotin or mevinolin type compounds have been highly evaluated owing to their strong inhibition of the production of cholesterol at the intermediate stage. However, since they inhibit the production of intermediary sterol compounds, they tend to reduce also the production of neurotransmitters and hormones which are essential for human body. Therefore, the use of this type of preparations are limited.

Poly unsaturated fatty acids are substances which would bring a preventive effect against arteriosclerosis only after a long period dosage. Also, their mild effects are overestimated without precise experiments as a pharmaceutical drug using pure single substance. With a decease of fish intake in Japan, the patients of hypohepatia, i.e., various hepatic diseases such as hepatocirrhosis, hepatocellular carcinoma, hepatitis and adipohepatia have increased so that it is desired to provide drugs for improving hepatic functions including a drug for removing cholesterol.

Hepatitis is caused by some viruses and various toxic substances, and brings hepatocytolysis. Especially, fulminant hepatitis brings severe subjective symptoms such as nausea, vomit, and cenesthopathia. It also brings clinical symptoms such as hyperthermia, hyperleukocytosis, crucially positive C-reactive protein and serious icterus, and sometimes causes death at the early stage. Even if the patient does not die, chronic hepatitis often moves to hepatocirrhosis and hepatocarcinoma, and brings many social problems.

For treating viral hepatitis such as A-type, B-type, C-type, O-type and E-type ones, it is proposed to dose interferons. However, the effects and appropriate dosage of interferons are not yet confirmed. Its combination with a steroid has also been tried but is reported to cause some adverse effects. Accordingly, the patients of hepatitis are at present treated mainly with a supplementary therapy, i.e., liver-protective therapy without any effective drug for hepatitis or any drug for inhibiting induction of hepatitis which accompanies no adverse effect (MEDICAL DIGEST, Vol. 39 (4), 1990).

Therefore, the object of the present invention is to provide an effective drug for improving hepatic functions and for treating and preventing hepatitis including fulminant hepatitis, hepatocirrhosis, hepatocellular carcinoma, and hepatic insufficiency with little toxicity.

DISCLOSURE OF INVENTION

The present inventors have continued to study on the constituents of marine organisms, mainly fishes, for a long period. Although some activities of poly unsaturated fatty acids were reported recently, the reported results were based on the experiments using not a single substance but uncertain various mixtures. Accordingly, the inventors first studied to produce highly pure poly unsaturated fatty acids, and, as a result, succeeded in the effective separation and purification of docosahexaenoic acid and its derivatives (hereinafter sometimes abbreviated as DHA) and filed a patent application which was opened to public as Japanese Patent Application Laid Open (Kokai) No. 4-95048. As a next stage, the inventors have tested on hepatic functions and hepatitis using pure DHA obtained according to an improved above separation and purification method, and have reached to unexpected results. Namely, the present invention have achieved based on the findings that DHA effectively inhibits the induction of hepatitis, and that DHA remarkably improves the maintenance and activation of functions of microsomes which contain various enzymes for detoxification and biosynthesis at liver.

Generally, hepatic functions are activated by improved flowability, i.e., flexibility and intensification of hepatic cell membrane and lipid bilayer of the microsome which is a granule in the cell. It is known that smaller cholesterol ratio relative to phospholipid enhances the flowability of the membranes, the phospholipid being a component of the lipid bilayer.

The drug for hepatic diseases according to the present invention contains docosahexaenoic acid and its derivatives (DHA) as the active ingredient. DHA includes DHA, esters of DHA, glycerides of DHA, phospholipids of DHA, and derivatives having enhanced water-solubility such as choline compounds of DHA, nicotinic acid compounds of DHA, and amino acid compounds of DHA. Preferred example as antihepatitis agent includes a triglyceride of DHA, which possesses a strong antihepatitis activity and is expected to exhibit therapeutical and preventive efficacy against hepatitis including fulminant hepatitis, hepatocirrhosis, hepatocarcinoma, hepatic insufficiency, etc.

DHA used in the present invention is commercially available and is also obtainable by extracting from animals, algae, and microorganisms in the nature according to known methods.

A preferable dosage of DHA, an active ingredient of the present drug, is in a range of 0.1 to 50 g/day, more preferably 0.5 to 10 g/day, with oral, intravenous, or enteral administration. The drug of the present invention may be formulated as tablets, capsules, granules, powder, liquid, etc. for oral administration. Parenteral administration can be performed with subcutaneous injection, intra-muscular injection, intravenous injection, suppository, or external medication.

The carrier for oral administration may be emulsifiers, vehicles, binders, lubricants, colorants, and the like which are usually used for pharmaceutical formulation. Examples of the vehicles include lactose, sucrose, starch, talc, magnesium stearate, crystalline cellulose, methyl cellulose, carboxymethyl cellulose, glycerol, sodium alginate, acacia, and the like. Examples of the binders include polyvinyl alcohol, polyvinyl ether, ethyl cellulose, acacia, shellac, sucrose, and the like. Other commonly used colorants, disintegrators, etc. can be also used. The tablets may be coated according to usual methods. Liquid preparations may be in the form of aqueous or oily suspension, emulsion, solution, syrup, or elixir which is formulated according to an usual method. The preparations for subcutaneous, intermusclar, or intravenous injection can be prepared by adding an emulsifier, a pH buffer, a stabilizer, an isotonic agent, a local anesthetic agent, etc. to DHA according to an usual method. The base material for suppository may be an oily one such as cacao butter, polyethylene glycol, lanolins, fatty acid triglycerides, witepsol, or the like.

In view of the smaller burden to patients, oral administration is most preferable for medication with DHA. Soft capsule preparations can be easily prepared simply by filling DHA optionally with 0.1 to 0.3% of dl-α-tocopherol or catechin as an antioxidant. Since one capsule suitably contains 100 to 1000 mg in total, 250 mg of docosahexaenoic acid and 0.5 mg of dl-α-tocopherol (or catechin) are sufficient to formulate into the soft capsule, for example. Otherwise, DHA can be mixed in various food materials or food itself, so that DHA will be provide in the form of daily foods or healthy foods.

Liquid preparations can be formulated with amino acid compounds or ascorbic acid compounds of DHA, or with aqueous or oily suspension, emulsifier, liposome, etc, optionally with pH buffer, a stabilizer, an isotonic agent, a local anesthetic agent, and the like. For example, 100 g of disodium docosahexaenoyl L-glutamate, 25 g of glycerol, and 0.1 g of dl-α-tocopherol are mixed with water so that the final volume becomes 1000 ml, and the solution is used as a liquid preparation after sterilization.

ACUTE TOXICITY TEST

Acute toxicity of ethyl docosahexaenoate was tested.
Tested animal: ddy-N mice, 5-week age, 5 male and 5 female
Result: $LD_{50} > 2000$ mg/kg (male and female)
All tested mice were anatomically evaluated after the test. No abnormal change on major organs of male and female mice were observed at any group after the DHA dosage of 160, 1380, 1660, or 2000 mg/kg.

BEST MODE FOR CARRYING OUT THE INVENTION

The efficacy of docosahexaenoic acid was demonstrated using its ethyl ester and triglyceride in the following examples. The effects shown in the examples can also be observed in the case that a phospholipid of DHA or ascorbate of DHA is used instead.

EXAMPLE 1

Four-week age, 18 male Sprague-Dowley rats were divided into 3 groups and were fed during 3 weeks freely with purified feed of AIN composition containing 10% fat for feed as described in the following table. In order to maintain the health and equality of the rats, the fat for feed was regulated to contain equal amount of saturated fatty acid, monounsaturated fatty acid, and polyunsaturated fatty acid (PUFA). Approximately 10% of the PUFA was n-3 type one, the remaining being n-6 type one. Ethyl esters of α-linolenic acid (ALA) and eicosapentaenoic acid (EPA) were used in comparative examples. Average daily intake of PUFA per a rat were 20.4 g at ALA group, 20.8 g in EPA group, and 21.3 g in DHA group.

| Feed Composition (%) | |
|---|---|
| Casein | 20 |
| Fats | 10 |
| Vitamin mixture (AIN) | 1 |
| Mineral mixture (AIN) | 3.5 |
| Choline tartrate | 0.2 |
| DL-Methionine | 0.3 |
| Cellulose | 5 |
| Corn starch | 15 |

Total percentage was made 100% with sucrose.

After 3 weeks, each rat was dissected and the lipid compositions of the blood plasma and liver were analyzed. The results are shown in the following table.

| | Lipids in Plasma and liver | | | | | |
|---|---|---|---|---|---|---|
| | Blood Plasma (mg/dl) | | | liver (mg/g) | | |
| | CHOL | TG | PL | CHOL | TG | PL |
| DHA | 57.0 ± 2.2 | 127 ± 18 | 299 ± 76 | 2.38 ± 0.13 | 10.6 ± 1.4 | 27.5 ± 0.5 |
| ALA | 80.9 ± 2.9 | 114 ± 17 | 356 ± 44 | 3.35 ± 0.27 | 20.5 ± 2.5 | 29.0 ± 0.6 |
| EPA | 71.3 ± 6.1 | 85 ± 14 | 366 ± 80 | 2.95 ± 0.14 | 13.6 ± 2.4 | 30.9 ± 0.7 |

In the table, CHOL means cholesterol, TG means triglyceride, and PL means phospholipid.

The result obviously showed that DHA reduced not only cholesterol level in both of liver and blood plasma, but also the level of triglyceride in liver, though DHA is seemingly less active in the reduction of triglyceride in blood plasma.

The following table shows analytical results of lipid in the membrane of hepatic microsome sampled according to a usual method.

| | Lipids in Hepatic Microsome | | |
|---|---|---|---|
| | CHOL | PL | CHOL/PL |
| | (nmol/mg-protein) | | ($\times 10^{-2}$) |
| DHA | 40.1 ± 4.0 | 464 ± 49 | 9.5 ± 1.9 |
| ALA | 44.3 ± 3.8 | 380 ± 63 | 14.1 ± 3.3 |
| EPA | 40.1 ± 2.2 | 376 ± 76 | 13.4 ± 3.1 |

In the table, CHOL and PL mean as above.

In the table, CHOL and PL mean as above.

At this test, DHA was observed to reduce cholesterol level specifically in the membrane of hepatic microsomes without damaging phospholipids which constitute the membrane. The table also shows a decrease of CHOL/PL ratio, which enhances flowability of the membranes of the microsomes so that hepatic cells are strengthened.

EXAMPLE 2

Male Wister rats of 200 g weight were processed to be model animals for inducing hepatitis. Namely, 1500 mg/kg-weight of D-galactosamine hydrochloride was intestinally administered and, at the same time, 10 μg of lipopolysaccharide derived from E. coli 0111:B$_4$ was injected intravenously. All of the model rats died within 24 hours appearing symptoms of induced fulminant hepatitis. On the contrary, 67% of the model rats survived more than 24 hours when an emulsion of DHA triglyceride containing 10% of 99% pure DHA triglyceride was administered simultaneously with the administration of the hepatitis inducer (D-galactosamine hydrochloride and lipopolysaccharide). This result indicates that DHA triglyceride inhibits the induction of hepatitis.

EXAMPLE 3

Instead of the emulsion of DHA triglyceride, an emulsion of ethyl ester of 99% pure DHA was administrated to the rats and the same experiment was conducted as in Example 2. In the experiment, 75% of the rats survived when ethyl ester of DHA was administrated, though 100% of control rats died within 24 hours.

INDUSTRIAL APPLICABILITY

While DHA participates the metabolism of cholesterol which appears in blood plasma, DHA specifically assists to metabolize cholesterol accumulated in hepatic microsomes when its metabolism has become weak or abnormal. As a result, flexibility of lipid membranes of the microsomes is recovered and enzymes are activated. Also, DHA significantly reduces neutral fats. Accordingly, DHA is promising to be a pharmaceutical remedy of adipohepatia and hepatocirrhosis which are difficult to be cured completely.

Furthermore, the present invention also provides an antihepatitis agent (a drug for hepatitis) which inhibits induction of hepatitis, one of the inducers of chronic hepatitis, hepatocirrhosis, hepatic insufficiency, and the like.

We claim:

1. A method for treating hepatitis comprising:
   administering to a subject in need of treatment for hepatitis an effective amount of docosahexaenoic acid or a docosahexaenoic acid (DHA) derivative selected from the group consisting of esters, glycerides, choline compounds of DHA, nicotinic acid compounds of DHA and amino acid compounds of DHA.

2. The method of claim 1 wherein said glyceride is a triglyceride.

* * * * *